United States Patent [19]

Pollak

[11] 4,449,938

[45] May 22, 1984

[54] ENDODONTIC FILLING AND SEALING COMPOSITION

[75] Inventor: Richard B. Pollak, Los Angeles, Calif.

[73] Assignee: Lee Pharmaceuticals, Inc., So. El Monte, Calif.

[21] Appl. No.: 350,404

[22] Filed: Feb. 19, 1982

[51] Int. Cl.$^3$ ............................................... A61K 6/08
[52] U.S. Cl. .................................... 523/116; 106/35; 260/998.11; 433/228; 523/117; 524/731; 528/18; 528/34; 528/901
[58] Field of Search ........................ 433/228; 106/35; 260/998.11; 523/115–118; 524/731, 901; 528/18, 34

[56] References Cited

U.S. PATENT DOCUMENTS

| | | | |
|---|---|---|---|
| 2,843,555 | 7/1958 | Berridge | 260/18 |
| 3,082,526 | 3/1963 | Nitzsche et al. | 32/15 |
| 3,127,363 | 3/1964 | Nitzsche et al. | 260/18 |
| 3,186,963 | 6/1965 | Lewis et al. | 260/46.5 |
| 3,897,376 | 7/1975 | Lampe | 260/18 S |
| 3,897,396 | 7/1975 | Ishii et al. | 260/75 NB |
| 3,957,704 | 5/1976 | Smith | 260/18 S |
| 4,007,123 | 2/1977 | Sheratte | 252/78.5 |

FOREIGN PATENT DOCUMENTS 841825  7/1960  United Kingdom .

*Primary Examiner*—Lorenzo B. Hayes
*Attorney, Agent, or Firm*—Joseph E. Mueth

[57] ABSTRACT

A biologically compatible non-toxic composition which when mixed, is useful as an in situ curing endodontic filling material. The composition has two separately packaged components. One component is a paste which contains a low viscosity hydroxy terminated polydialkylsiloxane and a non-reactive silicone oil diluent having a viscosity of from about 20 to 20,000 centistrokes at 25° C. and comprising a polydialkylsiloxane. The other component is a liquid which includes (i) the reaction product resulting from the refluxing at ambient pressure and a temperature of about 150° to about 175° C. under a nitrogen blanket in the absence of air and moisture a dialkyltindicarboxylate in which the alkyl groups have from 1 to about 8 carbon atoms and the carboxylate groups contain from about 10 to about 18 carbon atoms and a tetraalkyl orthosilicate, in the molar ratio of 1 to 3; (ii) uncombined alkyl orthosilicate and (iii) a non-reactive silicone oil diluent having a viscosity of from 20 to 120,000 centistrokes at 25° C. and comprising a polydialkylsiloxane.

The method of treating a root canal in need of endodontic filling which comprises the steps of forming a mixture by thoroughly mixing, with each 1.5 grams a paste component, 5 to 6 drops of the liquid component. The resulting mixture is injected by syringe or hypodermic needle into an endodontically prepared root canal and allowed to stand for about thirty minutes and harden in situ to form a flexible soft non-toxic filling material which conforms to the shape of the root canal cavity.

12 Claims, No Drawings

ENDODONTIC FILLING AND SEALING COMPOSITION

This invention relates to an endodontic filling and sealing composition. More specifically, the invention relates to a non-toxic, non-irritating endodontic filling and sealing composition which is inert to tooth structure and surrounding tissue which comprises a composition which is formed in situ in the root canal and which, prior to setting is of a viscosity enabling easy injection from a hypodermic needle.

BACKGROUND OF THE INVENTION

A practical endodontic filling composition has numerous requirements. It must not shrink excessively on setting, thus unsealing the root canal. It must set within a time which reasonably permits completion of endodontic procedure without undue patient discomfort. It must be biologically compatible with tooth structure and non-toxic. It must be inert to moisture and to the acid-base conditions found in the mouth. Is is preferably X-ray opaque. It should also be of low viscosity to facilitate ready insertion into and complete filling of the canal itself prior to setting. It should be easy to remove after setting if necessary or desirable. To permit insertion and retention in root canals of upper teeth before curing, it must be thixotropic. It should not discolor or stain tooth structure on prolonged residence in the mouth.

Systems which can be injected by means of a syringe have also been used as endodontic filling materials. One such system uses zinc oxide and eugenol. The two materials are mixed together to form a paste. This can be placed into a pressure syringe and injected into the root canal. The zinc oxide-eugenol mixtures polymerize when initiated by water. This material is a poor choice for several reasons. Adhesion to the walls of the canal is very low. It is very soluble and has little physical strength. It does not penetrate secondary canals.

A mixture of hydroxyethyl methacryate, fillers and catalysts has also been used as a syringeable endodontic filler since the monomer cures to a rigid plastic, which, after a few days, absorbs enough water to become a soft hydrogel. However, hydroxyethyl methacrylate is a serious skin irritant. The residual catalysts are also believed to be irritating. This material relies on the absorption of water to swell up and seal the canal so the seal is often incomplete.

Similarly, compositions based on epoxy resins have been employed as injectible endodontic filling materials. One such material, known as AH26, consists of an epoxy resin (diglycidyl ether of bisphenol A), fillers and hexamethylene tetramine. Although epoxy resin are generally considered to cure hard and rigid, this system cures slowly to a weak material. The epoxy resin is a bad skin irritant and sensitizer. The formaldehyde released in the presence of water by the breakdown of the hexamethylene tetramine is both an antiseptic and an irritant. Because of these drawbacks the material has not found widespread use.

Two part room temperature setting silicone compositions comprising a base material and a catalyst and the use thereof as dental impression material is described, for example, in U.S. Pat. Nos. 4,007,123 and 3,897,376. The base material of U.S. Pat. No. 4,007,123 comprises a hydroxy dimethyl siloxane, an organo-silicone cross-linker, and a unique filler, the catalyst component of which is a metal salt of a carboxylic acid, e.g., tin linoleate, stearate, oleate, acetate, or butyrate.

Two-component, room temperature setting organopolysiloxane compositions comprising (i) a hydroxy terminated diorganopolysilioxane mixed with a filler and (ii) a catalyst mixture of a tin carboxylate and an alkyl silicate or partially hydrolyzed alkyl silicate are described in U.S. Pat. No. 2,843,555. According to U.S. Pat. No. 3,897,396, it has been suggested that such two part compositions be placed in a syringe or other device and inserted from the device into the ear so that the composition can cure in situ to form an ear plug for the attenuation of sound.

Silicone compounds said to be useful as dental molding compounds and for filling tooth roots are described in British Pat. No. 841,825. U.S. Pat. No. 3,082,526 describes a single component, water or saliva cured silicone rubber system for filling root canals.

Silicone elastomers have been proposed for use as endodontic filling and sealing compositions. Such endodontic products so proposed were not formulated to enable application as a flowable liquid by a disposable syringe, e.g., a hypodermic syringe. Nor do prior writings concerning such proposals affirmatively show the achievement of a non-toxic root canal filling material inert to surrounding tissues and to mouth conditions, though it is to be recognized that such has necessarily been the desideratum.

For example, Nitzsche U.S. Pat. No. 3,127,363 describes a polysiloxane elastomer which cures at room temperature. The patent states that certain of the disclosed compositions are "especially suitable as root fillings for decayed teeth . . . because within a few minutes after having been pressed into the root channel they set to form a solid though still elastic mass . . . " (Col. 8, lines 33–40). Hydroxy terminated polysiloxanes are utilized as starting materials for polymerization with various metal salt catalysts incuding dibutyltin dicarboxylates. The Nitzsche patent discloses the use of cross-linking agents, but prefers such agents to be siloxanes present in relatively low amounts based on the weight of hydroxy terminated polysiloxane utilized. The patent discloses that "in certain circumstances" polyalkyl silicates may be used as cross-linkers (Col. 3, line 67–Col. 4, line 37), but lists numerous disadvantages connected with their use. In particular, greater shrinkage upon reaction of the hydroxy terminated polysiloxanes with cross-linkers is said to inhere if "polyethyl silicate" is the cross-linker than if $RSi(OX)_2$ or $RSi(OX)_3$ is so employed (Col. 4, lines 14–20). No particular formulation is exemplified as useful for root canal fillings. No reference is made to non-cross-linked compositions of a viscosity requisite to permit injection by syringe into the root canal. Some catalyst compositions of the type described in Nitzsche and the polymer obtained therefrom have been found to be biologically unacceptable.

Lewis U.S. Pat. No. 3,186,963 describes gelling a dimethyl polysiloxane at room temperature with a "vulcanizing agent" catalyst system which is a reaction product of a tin salt of carboxylic acid, e.g., dibutyl tin dilaurate and a silicate, e.g., ethyl orthosilicate. The reaction of the tin salt and the alkyl silicate is performed under ambient atmospheric conditions at 80° to 200° C. for at least 15 minutes, or under what the examples call "reflux" conditions using the same time and temperature criteria. The examples show that when an alkyl-polysilicate is substituted for ethylorthosilicate, the catalyst similarly prepared can be "diluted" with excess alkyl polysilicate, but Example 2 indicates that the gel time is lengthened when such "diluent" is present relative to an equivalent mix containing no diluent. No information is given with respect to the viscosity of the catalyst, diluted or undiluted, or of the dimethyl polysiloxane starting material. No information is given about the characteristics of the gelled composition. Nor is reference made to the use of the composition as a root canal filling and sealing material.

Smith U.S. Pat. No. 3,957,704 describes unique cross-linking agents for two component room temperature vulcanizable silicone rubber compositions. These cross-linking agents are said to solve certain problems which attend the compositions of Lewis U.S. Pat. No. 3,186,963; namely variation in the cure rate and instability of the activity of the catalyst component upon storage. Dilution of the Lewis reaction product catalyst with a non-reactive dimethylpolysiloxane chain stopped with triorganosiloxy units is said to degrade the catalyst component seriously in that the shelf life was less than one to two months.

BRIEF DESCRIPTION OF THE INVENTION

The present invention is a two component endodontic filling and sealing composition which is non-toxic, inert to tissues, including tooth tissues adjacent a root canal, inert to mouth conditions, non-discoloring upon aging, exhibits essentially no shrinkage upon curing and is of a viscosity prior to curing such that it can be placed in the root canal with a disposable syringe.

The essential ingredients of this novel filling and sealing composition are:

(1) a low viscosity hydroxy terminated polysiloxane of the general formula:

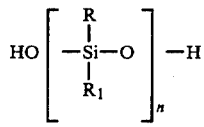
I.

wherein R and $R_1$, are each alkyl groups of from 1 to about 4 carbon atoms which may be the same or different and n is an integer of from about 8 to about 160;

(2) a catalyst prepared by reacting (a) a dialkyl tin dicarboxylate in which the alkyl groups have from 1 to about 8 carbon atoms and the carboxylate groups have from about 10 to about 18 carbon atoms with (b) tetraalkyl orthosilicate, by heating (a) and (b) in the molar ratio of 1 part (a) to about 3 parts of (b) under an atmosphere of nitrogen, and under conditions such that water and moisture are rigorously excluded, for at least about one hour at a temperature from about 150° to 175° C.;

(3) a biologically acceptable cross-linking agent, preferably ethyl orthosilicate. Uncombined tetraethyl orthosilicate is preferred;

(4) a fluid silicone oil having a viscosity of from about 20 to 120,000, preferably about 12,500 centistokes when measured at 25° C. comprising a di(lower alkyl) siloxane in which the alkyl groups have from 1 to about 3 carbon atoms—e.g., poly(dimethylsiloxane)—which functions at least mainly as a diluent.

X-ray opaquing agents such as barium sulfate, suitable pigments (e.g., zinc oxide; red iron oxide), fillers, medicaments, antioxidants, etc., may be included in the endodontic formulation as desired.

The endodontic filling and sealing material is formulated as two separately packaged components to be mixed immediately prior to injection into the root canal. A preferred system is one in which a base component comprising ingredient (1) is formulated as a paste composition which may also contain ingredient (4) as needed, desired pigments, X-ray opaquers, medicaments, etc., while ingredients (2), (3) and a further increment of (4), as needed, are formulated as a separate, liquid catalyst composition.

In the paste composition, the ingredient (1) is usually provided in an amount of 20 to 70% by weight of said paste, preferably 25–50% and even more preferably 30–40%. Ingredient (4) may be included in the paste in an amount up to about 70% by weight based on the weight of ingredient (1).

In the liquid, catalyst-containing composition, ingredient (2) constituting the catalyst comprises from about 5 to about 30%, preferably about 10–15% by weight of said liquid composition; ingredient (3), tetraalkyl orthosilicate, comprises from about 40% to about 60% by weight of the liquid composition, and preferably 50–55% by weight; and ingredient (4) comprises from about 15 to about 45%, by weight preferably about 30–35% by weight of the liquid composition.

In use, the two components are mixed in a ratio suitable to provide a low viscosity injectable liquid with a set time of about 20 to 60 minutes, injected into the prepared root canal, and allowed to set. Usually, about 5–6 drops of liquid catalyst composition, each of which weighs about 0.016 gram, are mixed with about 1.5 grams of paste to form a liquid that is readily injectable, suitably thixotropic and of proper set time to permit the dentist to perform any needed manipulations before the composition cures. About five to six drops of liquid catalyst composition are required for each 1.5 grams of paste to provide a mix with a working time of at least 30 minutes.

DETAILED DESCRIPTION OF THE INVENTION

The essential ingredients are first described in detail:

The Hydroxy Terminated Polysiloxane—Ingredient 1

Among the suitable hydroxy terminated polysiloxanes which are commercially available are a preferred type available from Mobay Chemical Corporation under the trade name Baysilone Polymer C. A Mobay "Product Information" bulletin states that "Baysilone Polymer C" is the name used for a group of polydimethylsiloxanes having terminal OH groups and the following general formula

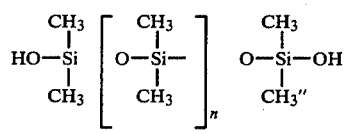

Baysilone Polymer C is available in various grades having a viscosity in centistokes at 20° C. as follows:

| Grade | C-0.7 | C2 | C5 |

| -continued | | | |
|---|---|---|---|
| Viscosity | 600–800 | 1800–2200 | 4000–6000 |

The lowest viscosity grade C-0.7 is preferred.

The Catalyst—Ingredient 2

The catalyst is prepared by heating a mixture of from about 20 to 80 weight percent of a dialkyl tin carboxylate and from about 80 to 20 weight percent of a tetraalkyl orthosilicate under reflux at about 150° to 175° C. atmospheric pressure for a time period of from one to four hours. It is essential for purposes of this invention that air and moisture be excluded during this reaction. Preferably the reaction is conducted under a nitrogen blanket. Preferably the catalyst reaction mixture contains, in substantially stoichiometric proportions, from about 35 to about 65 weight percent of dialkyl tin carboxylate and about 65 to about 40 weight percent of alkyl orthosilicate, i.e., about one mole dialkyl tin carboxylate for each three moles of ethyl orthosilicate.

The dialkyl tin carboxylate must be selected with care to avoid the formation of a carboxylic acid by-product which is an irritant or otherwise biologically unacceptable. For the purposes of this invention, dialkyl tin dilaurate is preferred. Other tin salts which yield biologically acceptable acid by-products include dialkyl tin oleate, linoleate, palmitate and stearate. Dialkyltindiacetate yields acetic acid, a toxic irritant, as a reaction by-product and hence does not provide a useful catalyst.

The alkyl orthosilicate is preferably selected to avoid the formation of a biologically unacceptable alcohol reaction product such as methyl alcohol but also to yield an alcohol reaction product which is absorbed without adverse effect in the cured endodontic filling. Alternatively the alcohol may be distilled off or vented after the catalyst reaction is completed. Tetraethyl orthosilicate is preferred. Tetra-n-propyl or tetra-n-butyl silicate or other suitable alkyl orthosilicates may be used.

The Cross-Linking Agent—Ingredient 3

A preferred cross-linking agent is uncombined tetraethyl orthosilicate. The ethyl alcohol by-product is non-toxic and is absorbed in the cured endodontic filling.

The Silicone Oil—Ingredient 4

The polydimethylsiloxane silicone oil ingredient is free of hydroxyl or other reactive end groups and does not participate in the curing reaction. Its purposes are many and include to dilute the catalyst to the desired concentration, to reduce viscosity of the combined base and catalyst mixture sufficiently to permit easy dispensing from a hypodermic needle, to reduce viscosity of the base composition, to protect the base and liquid compositions from moisture during storage, to plasticize the cured root canal filling, etc.

The preferred poly(dimethylsiloxane) oil is obtained as Dow Corning 360 Medical Fluid. The Dow Corning Corporation Medical Products Bulletin 51-374A dated May 1979 states that 360 Medical Fluid is a clear, colorless, polydimethylsiloxane liquid available in various viscosity grades including 20, 100, 350, 1000 and 12,500 cs at 25° C. For the purposes of this invention, the highest viscosity, 12,500 cs grade, is preferred. Other comparable poly(dimethylsiloxane) oils from other manufacturers may also be used so long as they are of appropriate viscosity.

Inert diluents other than polydimethylsiloxanes and which afford acceptable biological response may also be used. Industrial grades of silicone oils such as General Electric SF-69 are biologically unacceptable.

The silicone oil is utilized in an amount requisite to adjust the viscosity of the endodontic formulation to a level appropriate for syringe injection into the root canal.

Any excess of that required to provide an endodontic product of the desired viscosity is to be avoided to preclude undue flexibility and softness in the cured product. If more than about 50% by weight of silicone oil, based total weight, is present in the liquid component, its stability will be adversely affected.

Dilution with silicone oil also retards the rate of reaction between the base and catalyst components and impairs the flexibility of the cured product. For these reasons and to avoid bleeding of the diluent out on the surface of the cured mixture, no more than 50% weight percent of silicone oil based on ingredient 1 is utilized.

Flexibility of the cured endodontic filling and sealing composition is measured by mixing the base and catalyst components to form a paste and applying the paste with a 0.003 inch Bird Film applicator to a Q-Panel (a 3 inch×6 inch×0.01 inch tin-plated steel panel). After the paste is cured on the panel, the panel is bent over a ⅛ inch steel mandrel. If cracks appear visual to the eye, the material is said to fail the ⅛ inch bend test. Progressively larger mandrels may be used, if desired, to determine the size at which cracking does not occur.

Other Ingredients (Optional)

Other ingredients which may be included, as desired, are pigments, X-ray opaquers, medicaments, and thickening agents, cure retardants, cure accelerators, etc.

Pigments and X-ray opaquing agents, in general, also act as thickeners. Other additives may also perform dual functions in these formulations.

Among the pigments suitable for imparting a white color to the otherwise colorless cured root canal filling material of this invention are zinc oxide and titanium oxide, the first of which has a retardant effect upon initial set (or gelation) of the mix, thus allowing more working time to the endodontist, but an acceleration effect upon final cure. A preferred zinc oxide is U.S.P. No. 12 from New Jersey Zinc Division of Gulf and Western Industries. A preferred titanium dioxide is U.S.P. grade of about 0.3 micron average particle size.

When a flesh color is desired in the final product, red iron oxide may be added. A preferred form of this pigment is Atlas A6205 from H. Kohnstamm & Co., an approved drug and cosmetic color.

A preferred X-ray opaquing agent is natural barytes, such as Barytes 500 OC from Smith Chemical Co.

Care must be taken in selecting particulate additives that are so sized as not to clog the syringe used to place the mix in the root canal and that their properties are such that they do not tend to clump, but can easily be uniformly mixed.

In order to obtain a convenient setting time, and still insure a thorough cure, it is preferred to add up to 2 weight percent of a retardant comprising an alkanoic acid, preferably one with tail branching having from about 8 to 12 carbon atoms. The preferred alkanoic acid is neodecanoic acid. It has been found that alkanoic acids of too few carbon atoms impart odor problems to the mix during cure, whereas those with too many carbon atoms are uncompatible with the cured final composition and tend to bleed out.

EXAMPLE 1

Preparation of the Paste Component 211.5 grams of Mobay Baysilone Polymer C-0.7 is placed in a mixing bowl of a Hobart Mixer. 500.0 grams zinc oxide U.S.P., 150.0 grams barium sulphate and 3.2 grams synthetic red iron oxide were gradually added to the polymer under agitation. 135.3 grams of polydimethyl siloxane (Dow Corning 360 Medical Fluid, 20 cs) were gradually added to yield a paste. The paste is ground with two passes on a roller mill at the one dot position to obtain a No. 4 grind on the Hegman scale on a Precision Gauge and Tool Fineness of Grind Gauge, as specified in ASTM Method D1210. The paste was then strained through an 80 mesh nylon bag.

Preparation of the Liquid Catalyst Component

A mixture of 100 grams of dibutyl tin dilaurate and 100 grams of tetraethyl orthosilicate was reacted under reflux for two hours at a temperature of about 100° C. The reaction product was cooled and filtered through Whatman No. 1 paper. 133.2 gms of the reaction product catalyst was combined with 535.5 gms of tetraethyl orthosilicate and 330 gms of polydimethylsiloxane (Dow Corning 360 Medical Fluid, 20 cs).

Combination of the Liquid and Paste Components to Provide an Endondontic Filling Composition About 1.5 parts by weight of the paste component were combined with about 1 part by weight of the liquid catalyst component to provide a smooth thixotropic composition injectable into a root canal through a 30 gauge needle. This composition set in approximately 30–35 minutes to a smooth soft rubber characterized by a Shore A hardness of about 3. This cured product also readily passed the ⅛" mandrel bend test.

Injection of the Endodontic Composition Into a Root Canal

The root canal to be filled is cleansed and enlarged using traditional endodontic procedures. The canal is irrigated with sterile water and dried with paper points. Five drops of catalyst component (approximately 75 mg. reaction product of 0.21 millimoles of tetraethyl ortho silicate and 80.0 micromoles of dibutyl tin dilaurate), and 1.5 grams of base component (0.23 millimoles of Baysilone C-0.70) of paste are dispensed into a glass mixing slab. Since two moles of Baysilone C-0.70 react with one mole of tetraethyl orthosilicate there is twice as much cross linking agent as is stoichiometrically required. The liquid and paste are spatulated together until a uniform mix is obtained, about 30 seconds. This mixture is immediately inserted into a syringe and injected into the root canal. The canal is full when a small amount of the filling material appears at the preparation access. After about thirty minutes the material sets.

Variation in Liquid/Paste Ratio to Adjust Set Time

The practitioner can adjust the set time of the material by varying the ratio of catalyst to base used. Using the material from Example 1, the set time is varied according to the following table when used with 1.5 grams of the paste from Example 1.

| Drops Catalyst | Micromoles DBTDL | Millimoles TEOS | ADA Set Time at 23C* |
|---|---|---|---|
| 4 | 63.3 | .173 | 41 minutes |
| 5 | 79.1 | .216 | 24 |
| 6 | 95.0 | .259 | 18 |

*American National Standard Z165.19-1971 paragraph 4.3.4.
TEOS = Tetraethyl ortho silicate
DBTDL = Dibutyl tin dilaurate
One drop equals 0.017 grams of catalyst The use of less than 30 micromoles of dibutyl tin dilaurate and 0.08 millimoles of tetraethyl orthosilicate for each 0.21 millimoles of Baysilone C-0.70 yields a material which does not cure after 100 hours. If more than six drops, 95.0 micromoles of dibutyl tin dilaurate and 0.259 millimoles of tetraethyl orthosilicate are used, the material will set too quickly to be used in root canal treatment.

Increase in Cure Rate by Water Addition

Addition of a small amount of water to the mixture prepared in Example 1 does not significantly change the handling properties of the material but increases the cure rate and the thoroughness of the cure. To 1.50 grams of paste 0.00375 grams (0.208 millimoles) of distilled water was added. Set time was measured for material with varying amounts of catalyst at 23C and 37C.

| Drops Catalyst | Micromoles DBTDL | Millimoles TEOS | ADA Set Time 23C | ADA Set Time 37C |
|---|---|---|---|---|
| 2 | 31.6 | .086 | — | 121.0 min. |
| 3 | 47.5 | .130 | 44.5 min. | 27.4 |
| 4 | 63.3 | .173 | 22.5 | 14.5 |
| 5 | 79.1 | .216 | 19.2 | 12.1 |
| 6 | 95.0 | .259 | 15.0 | 8.1 |
| 7 | 110.8 | .302 | 10.3 | — |

| Moles B C-0.7/ Mole Water | Moles DBTDL Mole Water | Moles TEOS/ Mole Water | Set Time 37C |
|---|---|---|---|
| 0.9 | 0.152 | 0.413 | 121.0 min. |
| 0.9 | 0.228 | 0.625 | 27.4 |
| 0.9 | 0.304 | 0.832 | 14.5 |
| 0.9 | 0.380 | 1.04 | 12.1 |
| 0.9 | 0.456 | 1.24 | 8.1 |

A set time of less than fifteen minutes or more than sixty minutes will be difficult to use. In this example, water is added to the mixture in the proportion of 0.9 moles per mole of Baysilone C-0.70.

EXAMPLE 2

Preparation of the Paste Component 350 grams of Baysilone Polymer C-0.7 were combined in the bowl of a Hobart mixer gradually and with continuous stirring with 150.0 grams of titanium dioxide, 400 grams of barium sulfate, and 0.32 gram of red iron oxide. The paste so formed was ground with two passes on a three-roll mill to obtain at least a No. 4 grind as explained in Example 1. 90.03 grams of the ground product was combined with 9.97 grams of Polymer C-0.7, 0.10 grams of neodecanoic acid and 0.5 grams of deionized water. This mixture was stirred to provide a smooth homogeneous paste which was thereafter screened through an 80 mesh nylon screen.

Preparation of an Endodontic Filling and Sealing Material 15 parts of the paste component as described in this Example was combined with one part by weight of the liquid catalyst component as described in Example 1 but containing 12,500 gs silicone oil to produce a smooth thixotropic mass readily injectible through a 30 gauge needle. This product sets in approximately 35 minutes to a smooth soft rubber with cured properties similar to those of the cured product in Example 1.

The product of this Example 2 is a particularly preferred embodiment of the present invention.

EXAMPLE 3

85.33 grams of the ground paste described in Example 2 is mixed with 13.85 grams of Polymer C-0.7, 0.32 grams of fumed silica and 0.050 grams of distilled water to provide a smooth homogenous paste which is thereafter screened though an 80 mesh screen. A mixture of 15 parts of such paste with one part of the liquid catalyst component described in Example 1 provided a smooth thixotropic mass injectable through a 30 gauge needle which sets in approximately 45 minutes.

Biological Compatibility

The unmixed paste composition, the unmixed liquid composition, the freshly mixed but uncured total composition and the cured total composition have all been subjected to various tests on animals as detailed hereinafter. The various test methods employed are as follows:

(a) Mucous Membrane Irritation in Mice

The procedure was adapted from a test to examine the irritation potential of contraceptive preparations. The material is placed in the vaginas of virgin mice for 24 hours after which the tissue is examined microscopically for irritation response. All components of the endodontic filler were examined: the catalyst alone, the base alone, and the freshly mixed combination of the catalyst and base (implanted before polymerization).

(b) Muscle Implants in Rabbits

This procedure generally follows the USP procedure for muscle implants. The material is inserted using a hypodermic needle into the paravertebral muscles of the rabbit. Usually the test material was placed in three to four sites on one side of the spine and the control in a similar number of sites on the other side. The usual duration of the test was one week, although some were carried out for six weeks. After that time, the sites were exposed and examined for gross responses. In the latest testing histological studies of the tissue around the sites have also been conducted.

(c) Acute Toxicity in Mice

The procedure involves making standard size samples of polymerized material and extracting them in either normal saline or polyethylene glycol at prescribed temperatures and times. The extract is then injected either i.p. (in the abdominal cavity) or i.v. (in the blood stream) of mice. The animals are observed for toxic responses and survivors are sacrificed and subjected to autopsy. The USP sets standards for passing or failing the test.

(d) Hemolysis on Rabbit Blood

Again standard size samples are made and incubated with a diluted solution of rabbit blood in normal saline. After incubation, the saline solution is centrifuged and the supernatant examined spectrophometrically for red cell lysis. Standard controls are used and a percentage hemolysis of 5% or less is considered passing.

(e) Oral Toxicity (LD-50) in Mice

The oral toxicity test is a standard test procedure consisting of administering the material orally to mice and estimating the lethal dose for half the population. This test was not used as a screening test but for safety and handling information for the catalyst. The base was not examined because of the thick nature of the material and the general inactivity of the ingredients.

(f) Embryo Implants in Chickens

The procedure required 18 day old fertile chicken eggs. A "window" was cut in the egg and the test material implanted in the muscle of the embryo wing. The egg was then resealed and allowed to hatch (the hatch rate was also dependent on the material implanted). About 11 days after hatching the sites were examined grossly and histological preparations were made.

(g) Endodontic Usage Tests in Dogs or Rats

The endodontic usage tests were tests using dogs (and in one case rats) in which normal root canal preparations were made and after prescribed time periods, the periapical tissue was examined for irritation response.

(h) Open Epicutaneous Test or "OET" (Various Animals)

The OET (open epicutaneous test) consists of 21 daily topical applications followed by challenge applications for sensitization response.

(i) Guinea Pig Maximization Test ("GPMT")

This test consists of a one time injection of the material and an adjuvant plus a single topical application, followed by a two week "rest" before challenge for sensitization response.

Biological testing data is set forth in the ensuing table.

The following table summarizes biological tests conducted on the product of Example 1 or at least one of its components.

| Test Series | Type of Test | Material Tested | Summary Of Results |
|---|---|---|---|
| 599 | GPMT | Catalyst Component | In Progress |
| 598 | LD-50 (Mice) | Catalyst Component | In Progress |
| 597 | OET | Catalyst Component | In Progress |
| 594 | Chicken Implants | Fresh Mix | Moderate response in comparison to zinc oxide - eugenol (severe) and gutta percha (mild to none) |
| 591 | Hemolysis Implants | Cured Mix | Passed test in contrast to zinc oxide - eugenol which after one day's curing failed by large margin. |
| 589 | Muscle Implants | Fresh Mix | No adverse response seen by gross observation. In slides, mild to moderate |

-continued

| Test Series | Type of Test | Material Tested | Summary Of Results |
|---|---|---|---|
| 587 | Chicken Implants | Fresh Mix | response seen which compares favorably to mild response seen with U.S.P. plastic. Compared to zinc oxide - eugenol (worst response) and U.S.P. negative control plastic (mild response) showed moderate response (thin capsule, moderate infiltrate) |
| 576 | Muscle Implants | Fresh Mix | No adverse response seen macroscopically. Thin capsules and some infiltrate seen in histological preparations. |
| 571 | Rabbit Mucous Membrane Irritation | Catalyst Component | Compared to 70% ethanol, provoked very mild to no response |
| 568 | Muscle Implants | Fresh Mix | Neither implants with normal amount of catalyst nor those with twice normal amount provoked gross signs of irritation. Histology revealed mild response. |
| 567 | Modified Draize (Rabbits) | Base Component and Catalyst Component Separately | The base was not an irritant. The catalyst was mildly irritating |
| 477 | Endodontic Usage (dogs) | Mix | Compared to "Hydron" a commercial root canal filler of Kerr Co., provoked some moderate response with microabscesses, apparently resolving. |
| 470 | Antimicrobial activity | Base Component | 3 of 4 microorganisms inoculated into base were viable after 48 hours. |
| — | microscopic examination | Cured Mix | Compared favorably with "Hydron" when extracted teeth filled with each were examined under light and scanning electron microscopes. |
| 468 | Microbial inhibitor | Base Component, Catalyst Component and Cured Mix Separately Tested | None inhibited bacterial growth |
| 444 | Muscle Implants | Fresh Mix and Cured Mix each tested separately | Compared to "Hydron", which exhibited mild response, product of Example 1 showed no adverse response after 1 week. Photographs on file. |
| 442 | Hemolysis | Cured Mix | Compared to "Hydron" which showed 45.8% average hemolysis, Example 1 product showed 1.78% average hemolysis. |
| 437 | Hemolysis | Cured Mix (Normal catalyst amount and twice normal catalyst amount) | In U.S.P. and FDI test methods, average hemolysis for both bathes was less than 3%. |
| 434 | Extraction in Normal | Cured Mix | Passed U.S.P. Test in normal saline; |
| | saline and polyethylene glycol | | test in polyethylene glycol inconclusive and should be repeated. |
| 433 | Muscle Implants | Fresh Mix | No adverse tissue reaction after two and six weeks. Photographs on file. |

Human tests on the product of Example 1 are underway. The most notable ones are at the University of Missouri at Kansas City, Mo., one involving twenty patients in an 18 month controlled study; the other 20 patients over 12 months. Periodic recalls and reexaminations are ongoing in each study. Results so far are satisfactory.

As those of ordinary skill in the art will readily understand, a number of variations and adjustments are possible within the scope of this invention. It is accordingly not intended to limit the scope of the invention described unless the appended claims so require.

What is claimed is:

1. A biologically compatible non-toxic composition suitable, when mixed, as an in situ curing endodontic filling material which comprises two separately packaged components as follows:

(a) a paste component comprising a low viscosity hydroxy terminated polydialkylsiloxane and a non-reactive hydroxy-free silicone oil diluent having a viscosity of from about 20 to 20,000 centistokes at 25° C. and comprising a polydialkylsiloxane; and (b) a liquid component comprising (i) the reaction product obtained by refluxing at ambient pressure and a temperature of about 150° to about 175° C. under a nitrogen blanket in the absence of air and moisture (1) a dialkyltindicarboxylate in which the alkyl groups have from 1 to about 8 carbon atoms and the carboxylate groups contain from about 10 to about 18 carbon atoms and (2) a tetraalkyl orthosilicate, in the molar ratio of 1 to 3; (ii) uncombined alkyl orthosilicate and (iii) a non-reactive hydroxy-free silicone oil diluent having a viscosity of from about 20 to 120,000 centistokes at 25° C. and comprising a polydialkylsiloxane.

2. The material of claim 1 in which component (a) comprises about 20 to 70% by weight of hydroxy terminated polydialkylsiloxane and up to about 70% by weight based on the hydroxy terminated polydialkylsiloxane of silicone oil diluent and component (b) comprises about 5 to 30% by weight of said reaction product, about 40 to 60% by weight tetraalkyl orthosilicate and about 15 to 45% by weight silicone oil diluent.

3. The material of claim 2 in which component (a) comprises about 25 to 50% by weight of hydroxy terminated polydialkylsiloxane and about 50 to 70% by weight based on the hydroxy terminated polydialkylsiloxane of silicone oil diluent and component (b) comprises about 10 to 15% by weight of said reaction product, about 50 to 55% by weight tetraalkyl orthosilicate and about 30 to 35% by weight silicone oil diluent.

4. The material of claim 2 in which component (a) also contains at least one pigment and an X-ray opaquing agent.

5. The material of claim 4 in which the X-ray opaquing agent is barium sulfate.

6. The material of claim 4 in which zinc oxide is present as a pigment.

7. The material of claim 6 in which red iron oxide is also present as a pigment.

8. The material of claim 2 in which titanium dioxide is present as a pigment, and component (a) contains no silicone oil diluent.

9. The material of claim 8 containing an alkanoic acid of 8-12 carbon atoms as a retarder of initial setting of the total composition after mixing.

10. The material of claim 9 in which the alkanoic acid is neodecanoic acid.

11. The material of claim 10 in which red iron oxide is also present as a pigment.

12. The material of claim 1 packaged in kit form with component (a) in a compressible tube-type container and component (b) in a sealed bottle.

* * * * *